United States Patent
Shinagawa et al.

(10) Patent No.: US 9,517,221 B2
(45) Date of Patent: Dec. 13, 2016

(54) (2R)-2-PROPYLOCTANOIC ACID FOR FUNCTIONAL BRAIN DISEASE

(75) Inventors: Rika Shinagawa, Osaka (JP); Yoshifumi Kagamiishi, Osaka (JP); Taiji Shimoda, Nagasaki (JP)

(73) Assignee: ONO PHARMACEUTICAL CO., LTD., Osaka-shi (JP)

( * ) Notice: Subject to any disclaimer, the term of this patent is extended or adjusted under 35 U.S.C. 154(b) by 319 days.

(21) Appl. No.: 12/282,298

(22) PCT Filed: Mar. 8, 2007

(86) PCT No.: PCT/JP2007/054512
§ 371 (c)(1),
(2), (4) Date: Sep. 9, 2008

(87) PCT Pub. No.: WO2007/102571
PCT Pub. Date: Sep. 13, 2007

(65) Prior Publication Data
US 2009/0036529 A1    Feb. 5, 2009

(30) Foreign Application Priority Data
Mar. 9, 2006 (JP) ................. 2006-064831

(51) Int. Cl.
*A61K 31/20* (2006.01)
*A61K 45/06* (2006.01)

(52) U.S. Cl.
CPC ............... *A61K 31/20* (2013.01); *A61K 45/06* (2013.01)

(58) Field of Classification Search
CPC ..................................................... A61K 31/20
See application file for complete search history.

(56) References Cited

U.S. PATENT DOCUMENTS

2002/0032185 A1   3/2002  Itoyama et al.
2007/0078083 A1*  4/2007  Barlow .................. A61K 31/16
                                                 514/8.3

FOREIGN PATENT DOCUMENTS

| EP | 0632008 A1 | 1/1995 |
| JP | 2002-097158 A | 4/2002 |
| JP | 2005-247841 A | 9/2005 |
| JP | 2006016319 A * | 1/2006 |
| WO | 2005/032535 A1 | 4/2005 |
| WO | WO 2007130419 A2 * | 11/2007 |

OTHER PUBLICATIONS

JP 2006-016319; Jan. 2006; English machine translation.*
The National Institute of Mental Health (NIMH); "Depression"; 2008; NIH Publication No. 08 3561; accessed online Nov. 18, 2010; http://www.nimh.nih.gov/health/publications/depression/nimhdepression.pdf.*
Papakostas; "Dopaminergic-based pharmacotherapies for depression"; 2006; European Neuropsychopharmacology; 16: 391-402.*
Papakostas; "Dopaminergic-based pharmacotherapies for depression"; 2006; European Neuropsychopharmacology; 16: 391-402; PubMed abstract; PMID: 16413172.*
Kato et al.; "Arundic acid, an astrocyte-modulating agent, protects dopaminergic neurons against MPTP neurotoxicity in mice"; 2004; Brain Research; 1030: 66-73.*
CAS Registry No. 185517-21-9; accessed Apr. 11, 2014.*
Tateishi et al.; "Astrocytic Activation and Delayed Infarct Expansion After Permanent Focal Ischemia in Rats. Part II: Suppression of Astrocytic Activation by a Novel Agent (R)-(−)-2-propyloctanoic acid (ONO-2506) Leads to Mitigation of Delayed Infarct Expansion and . . . "; 2002; Journal of Cerebral Blood Flow & Metabolism; 22: 723-734.*
Lal et al.; "Effect of valproic acid on anxiety-related behaviors in the rat"; Brain Research Bulletin; vol. 5, Supplement 2, 1980, pp. 575-577; abstract.*
Margis et al.; "Changes in S100B cerebrospinal fluid levels of rats subjected to predator stress"; 2004; Brain Research 1028: 213-218.*
Asano et al.; "Arundic acid (ONO-2506) ameliorates delayed ischemic brain damage by preventing astrocytic overproduction of S100B"; 2005; Curr. Drug Targets CNS Neurol. Disord.; 4(2): 127-42; PubMed abstract; PMID: 15857298.*
Uys et al.; "Animal Models of Anxiety Disorders"; 2003; Current Psychiatry Reports; 5:274-281.*
Paulis, Tomas de "Ono-2506" Current Opinion in Investigational Drugs, Pharmapress, US, vol. 4, No. 7, Jan. 1, 2003, p. 863-867.
Helzel, Guenter et al. "The astroglial protein S100B and visually evoked event-related potentials before and after antidepressant treatment" Psychopharmacology, vol. 178, No. 2-3, Mar. 1, 2005, p. 161-166.
Schroeter, Matthias L. et al. "S100B is increased in mood disorders and may be reduced by antidepressive treatment" NeuroReport, vol. 13, No. 13, Sep. 16, 2002, p. 1675-1678.
European Search Report in counterpart European Application No. 07738003.8, dated Feb. 24, 2010.
Manev R, et al., Could treatment with arundic acid (ONO-2506) increase vulnerability for depression?, Med Hypotheses, 2006, vol. 67, No. 5; pp. 1170-1172, 'summary', p. 1171, left colum.
Rika Shinagawa, "Nokosoku Kyuseiki ni Okeru Astrocyte Tokuiteki Tanpaku S100 no Yakuwari", Folia Pharmacologica Japonica, 2006, vol. 127, No. 6, pp. 485 to 488.
Japanese Patent Office, Communication dated Sep. 4, 2012, in a counterpart Japanese application No. 2008-503903.

* cited by examiner

*Primary Examiner* — Timothy Thomas
(74) *Attorney, Agent, or Firm* — Sughrue Mion, PLLC

(57) ABSTRACT

[Problem to be solved]
Provision of an agent for preventing or treating a functional brain disease and/or inhibiting symptom development of the same.
[Means for solving the problems]
An agent for preventing or treating a functional brain disease and/or inhibiting symptom development of the same, which comprises (2R)-2-propyloctanoic acid or a salt thereof.
The agent for preventing or treating a functional brain disease and/or inhibiting symptom development of the same, which comprises (2R)-2-propyloctanoic acid or a salt thereof, can be safely administered to patients of, for example, functional brain diseases such as depression, menopausal mood disorder, perimenopausal mood disorder, panic disorder, irritable bowel syndrome, social anxiety disorder, post-traumatic stress disorder or the like, and also can show excellent effects.

4 Claims, No Drawings

(2R)-2-PROPYLOCTANOIC ACID FOR FUNCTIONAL BRAIN DISEASE

This is a national stage application of PCT/JP2007/054512 filed on Mar. 8, 2007, which claims priority from Japanese patent application 2006-064831 filed on Mar. 9, 2006, all of which are incorporated herein by reference.

TECHNICAL FIELD

The present invention relates to an agent for preventing or treating a functional brain disease and/or inhibiting symptom development of the same, which comprises (2R)-2-propyloctanoic acid or a salt thereof.

BACKGROUND OF THE INVENTION

In general, according to whether lesion is found in the cranial nerve tissue, diseases of the brain are roughly divided into organic brain diseases and functional brain diseases. It is considered that the functional brain diseases among them, in which an organic change (lesion) is not found in cranial nerve tissues, are induced by a certain functional disorder of the brain, unbalance of the cerebral neurotransmitter or an environmental factor or genetic factor.

The number of patients of depression and anxiety disorders as typical functional brain diseases has been increasing every year, and various drugs for their treatment have also been developed. For example, a tricyclic antidepressant, a tetracyclic antidepressant, a monoamine oxidase (MAO) inhibitor, a serotonin and noradrenaline reuptake inhibitor (SNRI), a selective serotonin reuptake inhibitor (SSRI) or the like are used in the treatment of depression. However, problems to be improved are recognized in these drugs, such as their insufficient therapeutic effect, requirement for a prolonged period of time until the onset of their effects, or appearance of side effects including sleepiness, thirst, constipation, difficulty of urination or the like. Additionally, a benzodiazepine, thienodiazepine, non-benzodiazepine drugs or the like are used in the treatment of anxiety disorders. However, problems are also recognized in these drugs, such as insufficient therapeutic effect, or lowering of psychomotor function, lowering of concentration and attentiveness, sleepiness, dizziness, vertigo, headache, amnesia or the like.

On the other hand, it has reported that 2-propylpentanoic acid derivatives including (2R)-2-propyloctanoic acid are useful as a therapeutic and/or preventive agent for neurodegenerative diseases, neural function disorders after stroke or cerebrospinal injury, cerebrospinal diseases accompanied by cerebral tumor or infection or the like since it they have astrocyte function improving activity (e.g., see European Patent No. 0632008 (Patent Document 1).

Also, it has been reported that said 2-propylpentanoic acid derivatives are useful as a therapeutic and/or preventive agent for Parkinson disease or parkinsonian syndrome (e.g., see European Patent Publication No. 1174131 (Patent Document 2)).

Additionally, it is reported also that (2R)-2-propyloctanoic acid is useful as a nerve regeneration accelerator for the treatment and/or prevention of various neurodegenerative diseases (e.g., see International Publication No. 2005/032535 (Patent Document 3)).

However, all of these diseases described in conventionally known references are diseases which accompany organic changes of cranial nerve tissues such as nerve cell degeneration, and so far there is no case reporting that (2R)-2-propyloctanoic acid is effective for a functional brain disease which does not accompany organic changes of cranial nerve tissues.

[Patent Document 1] European Patent No. 0632008
[Patent Document 2] European Patent Publication No. 1174131
[Patent Document 3] International Publication No. 2005/032535

DISCLOSURE OF THE INVENTION

Problems to be Solved by the Invention

The problem of the present invention is to provide a safe agent having excellent therapeutic effect for functional brain diseases represented by depression, anxiety disorder or the like.

Means for Solving the Problems

With the aim of solving the above-mentioned problem, the inventors of the present invention have conducted intensive studies and found as a result that, to our surprise, the (2R)-2-propyloctanoic acid known to be useful in the treatment of organic brain diseases also has an excellent therapeutic effect for functional brain diseases, and accomplished the present invention by further minutely carrying out studies based on this knowledge.

Namely, the present invention relates to [1] an agent for preventing or treating a functional brain disease and/or inhibiting symptom development of the same, which comprises (2R)-2-propyloctanoic acid or a salt thereof; [2] the agent according to the aforementioned [1], which comprises from about 1 mg to about 5000 mg of (2R)-2-propyloctanoic acid or a salt thereof, [3] the agent according to the aforementioned [1], wherein the functional brain disease is a mood disorder and/or an anxiety disorder; [4] the agent according to the aforementioned [3], wherein the functional brain disease is depression, menopausal mood disorder, perimenopausal mood disorder, panic disorder, irritable bowel syndrome, social anxiety disorder and/or post-traumatic stress disorder; [5] the agent according to the aforementioned [1], which is used in combination with one or more species selected from an anxiolytic drug, an antidepressant, an antiparkinsonian drug, an antischizophrenic agent, an antiepileptic agent, an antidinic agent, an antiasthmatic agent, an antiulcer agent, a digestive organ function controlling agent, a digestive tract movement enhancer, an antidiarrheal drug, a purgative, a hypotensive drug, an antiarrhythmic drug, an inotropic agent and an agent for treating urinary disturbance; [6] a method for preventing or treating a functional brain disease and/or inhibiting symptom development of the same, which comprises administering an effective amount of (2R)-2-propyloctanoic acid or a salt thereof to a mammal; and [7] use of (2R)-2-propyloctanoic acid or a salt thereof for the manufacture of an agent for preventing or treating a functional brain disease and/or inhibiting symptom development of the same.

In the present invention, (2R)-2-propyloctanoic acid is a compound represented by formula (I):

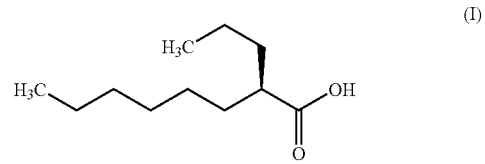

wherein ⫽ represents that it is a β-configuration.

In the present invention, it is preferable that the salt of (2R)-2-propyloctanoic acid is a pharmaceutically acceptable salt. A preferable pharmaceutically acceptable salt is non-toxic and water-soluble salt. Examples of the suitable salt of (2R)-2-propyloctanoic acid include a salt with an inorganic base, a salt with an organic base, a salt with a basic natural amino acid or the like. As the salt with an inorganic base, for example, an alkali metal salt (e.g., sodium salt, potassium salt, lithium salt or the like), an ammonium salt (e.g., tetramethylammonium salt, tetrabutylammonium salt or the like) or the like are preferable. As the salt with an organic base, for example, salts with an alkylamine (e.g., methylamine, dimethylamine, trimethylamine, triethylamine or the like), a heterocyclic amine (e.g., pyridine, picoline, piperidine or the like), an alkanolamine (e.g., ethanolamine, diethanolamine, triethanolamine or the like), dicyclohexylamine, N,N'-dibenzylethylenediamine, cyclopentylamine, benzylamine, dibenzylamine, phenethylamine, tris(hydroxymethyl)methylamine, N-methyl-D-glucamine or the like are preferable. Although the salt with a basic natural amino acid is not particularly limited as long as it is a salt with basic amino acid which is naturally distributed and can be purified, for example, a salt with arginine, lysine, ornithine, histidine or the like is preferable.

The (2R)-2-propyloctanoic acid or a salt thereof can be produced in accordance with the conventionally known methods, for example, the methods described in European Patent No. 0632008, International Publication No. 99/58513, International Publication No. 00/48982, Japanese Patent No. 3032447, Japanese Patent No. 3084345, International Publication No. 2003/051852, International Publication No. 2003/097851, International Publication No. 2004/092113, International Publication No. 2004/110972, International Publication No. 2005/105722 and the like, similar methods thereof, or the methods described in "Comprehensive Organic Transformations: A Guide to Functional Group Preparations, $2^{nd}$ Edition (Richard C. Larock, John Wiley & Sons Inc., 1999)", or by optionally combining these methods. The reaction product can be purified by general purification methods such as distillation under ordinary pressure or under a reduced pressure, a high performance liquid chromatography, thin layer chromatography or column chromatography which uses silica gel or magnesium silicate, washing, recrystallization or the like. In addition, if necessary it may be subjected to the process such as freeze-drying or the like.

The (2R)-2-propyloctanoic acid or a salt thereof to be used in the present invention is not limited to a substantially pure and single substance, and may contain impurities (e.g., by-products derived from production process, solvents, materials or the like, or degradation products) as long as they are within the acceptable range as pharmaceutical bulk. The impurity content acceptable as pharmaceutical bulk varies depending on whether (2R)-2-propyloctanoic acid is used or a salt thereof is used, and also varies depending on the contained impurities. For example, in the case of (2R)-2-propyloctanoic acid, it is preferable that heavy metals (e.g., lead, bismuth, copper, cadmium, antimony, tin, mercury or the like) are about 20 ppm or less, an optical isomer S-form is about 1.49% by mass or less, the residual solvents 2-propanol and heptane are about 5000 ppm or less in total, and the moisture is about 0.2% by mass or less. As the (2R)-2-propyloctanoic acid to be used in the present invention, particularly a (2R)-2-propyloctanoic acid having an optical purity of exceeding about 99% e.e., in particular a (2R)-2-propyloctanoic acid having an optical purity of 99.3% e.e. or more, is preferable.

The present invention discloses a method for preventing or treating a functional brain disease and/or inhibiting symptom development of the same, which comprises administering an effective amount of (2R)-2-propyloctanoic acid or a salt thereof to a mammal (e.g., human and non-human (e.g., monkey, sheep, cattle, horse, dog, cat, rabbit, rat, mouse or the like)), preferably a human (a patient) (hereinafter, sometimes abbreviated to the method of the present invention), and an agent for preventing or treating a functional brain disease and/or inhibiting symptom development of the same (hereinafter, sometimes abbreviated to the agent of the present invention) to be used in such method. In this connection, the "prevention" according to the present invention means to prevent generation of a functional brain disease or to keep it at a first-degree symptom when it is occurred; the "treatment" means to alleviate the functional brain disease; and the "symptom development inhibition" means to stop acceleration of symptoms of the functional brain disease. Additionally, for example, a meaning of suppressing generation of the following attacks in functional brain diseases in which attacks are generated periodically or irregularly is included in "prevention".

According to the present invention, the functional brain disease may be any disease in which lesions (organic changes) such as degeneration of nerves or the like are not found in the cranial nerve tissues. Examples of the functional brain disease include somatoform disorders [e.g., somatization disorder, conversion disorder, hypochondriasis, pain disorder, somatic ugly form disorder, somatoform autonomic dysfunction, persistent somatoform pain disorder or the like], anxiety disorders [e.g., panic attack, panic disorder (episodic paroxysmal anxiety), phobia (phobic anxiety disorder) (e.g., acrophobia, claustrophobia, tip phobia, agoraphobia, social phobia (social anxiety disorder), specific (isolated) phobia or the like), anankastic disorder (e.g., compulsive thinking, recurrent thing, threatening behavior (threatening rite), mixed compulsive thinking, threatening behavior or the like), stress related disorder (e.g., post-traumatic stress disorder (PTSD), acute stress disorder, stress-induced immunosuppression, stress-induced headache, stress-induced fever, stress-induced pain, operative stress, gastrointestinal disorder associated with stress, irritable bowel syndrome or the like), adjustment disorder (e.g., emotional disturbance, conduct disorder, disorder with both of them, somatic complaint, social withdrawal, occupational or study hitch or the like), neurasthenia, derealization syndrome, generalized anxiety disorder, mixed anxiety depression disorder, anxiety by a somatic disorder or substance or the like], dissociation disorders [e.g., dissociated amnesia, dissociated fugue (fugue), dissociated stupor, trans and possession disorder, dissociated movement disorder, dissociated spasm, dissociated numbness and anesthesia, mixed dissociation disorder, dissociated identity disorder, depersonalization disorder or the like], mood disorders [e.g., depression (e.g., major depression, mild depression, moderate depression, severe depression without psychotic symptoms, severe depression with psychotic symptoms or an episode thereof, single episode depression, recurrent depression, postpartum depression, child abuse induced depression, senile depression, masked depression, seasonal depression or the like), mania (e.g., hypomania, mania without psychotic symptoms, mania with psychotic symptoms or an episode thereof or the like), bipolar disorder (e.g., hypomanic episode, mania episode without psychotic symptoms, mania episode with psychotic symptoms, mild or moderate depression episode, severe depression episode without psychotic symptoms, severe depression episode with psychotic symptoms, mixed episode, the one under remission or the like), recurrent depression disorder (e.g., mild episode, moderate episode, severe episode without psychotic symptoms, severe episode with psychotic symptoms, the one under remission or the like), dysthymic disorder, cyclothymic disorder, single affective disorder, recurrent affective disorder, indefinite complaint, premenstrual dysphoria disorder, postpartum mood disorder, perimenopausal mood disorder, menopausal mood disorder or the like], suicidal behavior, self-mutilation, personality disorder [e.g., delusional personality disorder, schizoid personality disorder, dissocial personality disorder, emotional unstable personality disorder, impulse personality disorder, borderline personality disorder, other emotional instability personality disorder, histrionic personality disorder, anankastic personality disorder, anxiety (avoidant) personality disorder, dependent personality disorder, enduring personality change, pathological gambling, pathological arson (pyromania), pathological theft (kleptomania), trichologia or the like], mental-sexual disorder [e.g., sexual dysfunction (e.g., hypoactive sexual desire disorder, sexual aversion disorder, sexual dysfunction due to somatic disorder, substance induced sexual dysfunction, orgasm dysfunction, premature ejaculation, nonorganic vaginismus, nonorganic dyspareunia, hypersexuality, puerperal psychosis or the like), gender identity disorder (e.g., transsexualism, bisexual role transvestitism or the like), paraphilia (e.g., fetishism, fetishismic transvestitism, pedophilia, exhibitionism, inspectionism, sexual masochism, sexual sadism or the like) or the like], drug dependence [e.g., alcohol dependence, dependency on opioids, dependency on anxiolytic, sedative or hypnotic drugs, dependency on cannabis (marihuana), dependency on cocaine, dependency on amphetamine, dependency on other psychoanaleptic drugs including caffeine, dependency on hallucinogenic drug, dependency on phencyclidine, dependency on cigarette, dependency on volatile solvents, use of volatile nitrate or the like and behavioral disorders associated therewith (e.g., acute intoxication, noxious use, dependency syndrome, state of withdrawal, state of withdrawal with delirium, psychotic disorder, amnestic syndrome, residual and late psychotic disorders, other mental and behavioral disorders or the like) or the like], eating disorder [e.g., anorexia nervosa, atypical anorexia nervosa bulimia nervosa, atypical bulimia nervosa, absurd eating disorder, hyperorexia, nervous vomiting or the like], nonorganic sleep disorder [e.g., nonorganic insomnia, nonorganic hypersomnia, nonorganic sleep-wake schedule disorder, sleepwalking disease (somnambulism), sleep terrors (night terrors), nightmare, fibromyalgia sleep disorder or the like], Munchhausen's syndrome, intellectual disorder (mental retardation) [e.g., mild, moderate, severe, profound and other intellectual disorders (mental retardation) or the like], mental development disorder [e.g., specific development disorder of talk and language (e.g., specific talk dysarthria, expressive speech disorder, receptive speech disorder, acquired aphasia with epilepsy (Landau-Kleffner syndrome) or the like), specific development disorder of learning ability (e.g., specific dyslexia, specific dysgraphia, specific disorder of arithmetic ability, mixed disorder of learning ability or the like), specific development disorder of motor function, mixed specific development disorder, pervasive developmental disorder (e.g., autism, atypical autism, Rett syndrome, other child (childhood) disintegration disorder, hyperkinetic disorder related to intellectual disorder (mental retardation) and stereotypical of movement, Asperger syndrome or the like), other mental development disorders, or the like], behavioral and emotional disturbance which is generally developed at the child (juvenile) stage and adolescent stage [e.g., hyperactivity disorder (e.g., attention deficit hyperactive disorder, hyperkinetic conduct disorder or the like), conductive disorder (e.g., family localized conduct disorder, anti-social (anti-grouping) conduct disorder, social (grouping) conduct disorder, oppositional and defiant disorder or the like), disturbance of emotions and conduct (e.g., depressive conduct disorder or the like), emotional disorder which is specifically developed at the child (juvenile) stage (e.g., separation anxiety disorder at the child (juvenile) stage, phobic anxiety disorder at the child (juvenile) stage, sociability anxiety disorder at the child (juvenile) stage, sibling rivalry disorder or the like), social function disorder which is specifically developed at the child (juvenile) stage and adolescent stage (e.g., selective mutism, reactive attachment disorder at the child (juvenile) stage, disinhibition attachment disorder at the child (juvenile) stage, tic disorder, transient tic disorder, chronic motor or vocal tic disorder, a tic disorder which includes both of vocal and multiple motor (Gilles de la Tourette syndrome) or the like), other disturbance of emotions and conduct which is specifically developed at the child (juvenile) stage and adolescent stage (e.g., nonorganic enuresis, nonorganic encopresis, suckling disorder at the infant stage and child (juvenile) stage, pica at the infant stage and child (juvenile) stage, stereotypic movement disorder, stuttering, cluttering speech disorder or the like) or the like] and the like. As the functional brain diseases among these various diseases, for example, mood disorders, anxiety disorders or the like are suitable, and particularly, depression, menopausal mood disorder, perimenopause mood disorder, panic disorder, irritable bowel syndrome, social anxiety disorder, post-traumatic stress disorder or the like are more suitable.

When (2R)-2-propyloctanoic acid or a salt thereof is used in preventing or treating above-mentioned disease and/or inhibiting symptom development of the same, its route of administration may be either an oral administration or a parenteral administration. The parenteral administration may be, for example, a systemic administration such as intravenous administration, or for example, a topical administration such as intrathecal administration, percutaneous administration or the like. Dose of the (2R)-2-propyloctanoic acid or a salt thereof may be any dose as long as it is a dose which shows the efficacy for the aforementioned diseases without significant toxicity of (2R)-2-propyloctanoic acid or a salt thereof. In general, it is used within the range of from about 1 mg to about 5000 mg. In this connection, when the administration method is changed as described in the above, the dose necessary for obtaining desired effect is also changed, so that a suitable dose may be selected according to the administration method, when (2R)-2-propyloctanoic acid or a salt thereof is administered. Regarding the rough indication of the dose of (2R)-2-propyloctanoic acid or a salt thereof, for example, when (2R)-2-propyloctanoic acid or a salt thereof is orally administered, the dose of (2R)-2-propyloctanoic acid or a salt thereof per once is preferably from about 50 mg to about 5000 mg, more preferably from about 100 mg to about 2000 mg, particularly preferably from about 300 mg to about 1500 mg. Also, for example, when (2R)-2-propyloctanoic acid or a salt thereof is intravenously administered, the dose of (2R)-2-propyloctanoic acid or a salt thereof per once is preferably from about 50 mg to about 2000 mg, more preferably from about 100 mg to about 1500 mg, particularly preferably from about 150 mg to about 1200 mg. Also, for example, when (2R)-2-propyloctanoic acid or a salt thereof is intrathecally administered, the dose of (2R)-2-propyloctanoic acid or a salt thereof per once is preferably from about 1 mg to about 1000 mg, more preferably from about 1 mg to about 500 mg, particularly preferably from about 10 mg to about 500 mg. Additionally, for example, when (2R)-2-propyloctanoic acid or a salt thereof is percutaneously administered, the dose of (2R)-2-propyloctanoic acid or a salt thereof per once is preferably from about 1 mg to about 500 mg, more preferably from about 1 mg to about 50 mg. In this connection, when a salt of (2R)-2-propyloctanoic acid is used, the dose described in the above as the amount of (2R)-2-propyloctanoic acid is suitable.

Particularly, when (2R)-2-propyloctanoic acid or a salt thereof is intravenously administered, it is preferable to define its dose based on the body weight of a mammal (e.g., a human, a non-human animal or the like, preferable a human (a patient)), in order to obtain a suitable effect for preventing or treating the aforementioned functional brain disease and/or inhibiting symptom development of the same. In the case of a patient, for example, it is preferable to administer for example from about 1 mg to about 20 mg or the like of it, and it is more preferable to administer from about 2 mg to about 18 mg or the like of it, per 1 kg body weight of the patient. Examples of more illustrative dose include about 2 mg, about 4 mg, about 6 mg, about 8 mg, about 10 mg, about 12 mg, about 15 mg or about 18 mg or the like, per 1 kg body weight of a patient. Examples of more preferable dose include about 4 mg, about 6 mg, about 8 mg, about 10 mg or about 12 mg or the like per 1 kg body weight of a patient. Particularly, examples of the most preferable dose include about 8 mg or about 10 mg or the like per 1 kg body weight of a patient can be cited.

Additionally, when the (2R)-2-propyloctanoic acid or a salt thereof is intravenously administered, it may be given by one shot rapid intravenous injection or by intravenous continuous administration (preferably intravenous infusion) using a syringe, infusion bag or the like. By carrying out the continuous administration, it becomes possible to avoid side effects accompanied by the rapid increase of its blood concentration. As occasion demands, it is also possible to control the blood concentration or the like. In the case of carrying out continuous administration, although the period of time spending for the administration is not particularly limited and may be changed depending on the condition of a mammal (e.g., a human, a non-human animal or the like, preferable a human (a patient)) and other reasons, for example, it is preferably from about 0.5 hour (about 30 minutes) to about 3 hours (about 180 minutes), preferably from about 0.5 hour (about 30 minutes) to about 1.5 hours (about 90 minutes), particularly preferably about 1 hour (about 60 minutes), per one administration.

When the (2R)-2-propyloctanoic acid or a salt thereof is administered to a mammal (e.g., a human, a non-human animal or the like, preferable a human (a patient)) by the above-mentioned administration method, a pharmaceutical composition is used according to the respective administration form.

For example, pharmaceutical compositions to be used for the administration by injection (e.g., intravenous administration, intrathecal administration or the like), so-called transfusions, injections or the like, can be produced by dissolving (2R)-2-propyloctanoic acid or a salt thereof and metal salts generally used in injections (e.g., sodium triphosphate, disodium hydrogen phosphate, sodium carbonate, sodium sulfite or the like) and a pH adjusting agent (e.g., sodium hydroxide or the like), as well as additives such as a stabilizer, a surfactant agent, a buffering agent, a solubilizer, an antioxidant, an antifoaming agent, a tonicity agent, an emulsifying agent, a suspending agent, a preservative, a soothing agent, a dissolving agent, a solution adjuvant and the like which are described for example in "Iyakuhin Tenkabutsu Jiten" (edited by The Japanese Society of Pharmaceutical Additives) published in 2000 by Yakuji Nippo Sha, in a solvent (e.g., distilled water for injection or the like). Also, in the case of transfusions, in addition to these additive agents, components generally used in transfusions such as electrolytes (e.g., sodium chloride, potassium chloride, calcium chloride, sodium lactate, sodium dihydrogenphosphate, sodium carbonate, magnesium carbonate or the like), saccharides (e.g., glucose, fructose, sorbitol, mannitol, dextran or the like), protein amino acids (e.g., glycine, aspartic acid, lysine or the like) and vitamins (e.g., vitamin B1, vitamin C or the like) and the like can also be used. Such a pharmaceutical composition is produced and prepared by sterilizing at the final step or by an aseptic processing. Additionally, it can also be used by producing a sterile preparation, such as a freeze-dried preparation, and dissolving it in sterilized or aseptic sterilized purified water or other solvent, prior to its use.

Additionally, for example, the pharmaceutical compositions to be used in oral administration, so-called oral administration preparations, may be in any dosage forms as long as these can be orally administered to a mammal (e.g., a human, a non-human animal or the like, preferable a human (a patient)). As the oral administration preparation to be used in the present invention, which comprises (2R)-2-propyloctanoic acid or a salt thereof, for example, tablets, capsules, fine subtilaes, granules, powders or the like are preferable, and particularly capsules, in particular soft capsules are preferable. For example, preparations such as tablets, fine subtilaes, granules and powders can be produced using (2R)-2-propyloctanoic acid or a salt thereof and a generally used excipient (e.g., sucrose, lactose, glucose, starch, mannitol, sorbitol, cellulose, talc, cyclodextrin or the like), a binder (e.g., cellulose, methyl cellulose, polyvinyl pyrrolidone, gelatin, gum arabic, polyethylene glycol, sucrose, starch or the like), a disintegrating agent (e.g., starch, carboxymethylcellulose, calcium salt of carboxymethylcellulose or the like), a lubricant (e.g., talc or the like) and the like. Also, for example, soft capsules can be produced by coating (2R)-2-propyloctanoic acid or a salt thereof with a generally used capsule shell. The capsule shell can be produced using a capsule base [e.g., a protein (e.g., gelatin, collagen or the like), a polysaccharide (e.g., starch, amylose, polygalacturonic acid, agar, carrageenan, acacia, gellan gum, xanthan gum, pectin, alginic acid or the like), a biodegradable plastic (e.g., polylactic acid, polyhydroxybutyric acid, polyglutamic acid or the like), hydrogenated fat (e.g., triglyceride and diglyceride of a middle-chain fatty acid or the like) or the like] and a plasticizer [e.g., a saccharide (e.g., simple sugar, sucrose, starch syrup or the like), a sugar alcohol (e.g., sorbitol, xylitol, mannitol or the like), a polyhydric alcohol (e.g., glycerol, ethylene glycol, polyethylene glycol, propylene glycol or the like) or the like] as essential components, and using, as occasion demands, an aroma chemical (e.g., peppermint oil, cinnamon oil, fruit essence and flavor of strawberry or the like, or the like), an antiseptic (e.g., ethyl p-hydroxybenzoate, propyl p-hydroxybenzoate or the like), a pigment (e.g., Yellow No. 4, Yellow No. 5, Red No. 3, Blue No. 1, copper chlorophyllin or the like), an opaquer (e.g., titanium dioxide, red iron oxide or the like), a solubility adjusting agent (e.g., cellulose acetate phthalate, an alkali metal salt of hydroxypropylmethylcellulose, an alkali metal salt of hydroxymethylcellulose acetate succinate, alginic acid alkali salt, polyacrylic acid alkali metal salt, methyl cellulose, carboxymethylcellulose, casein, collagen, agar powder, polyvinyl alcohol, pectin or the like) and the like.

Additionally, the pharmaceutical composition to be used in percutaneous administration, so-called percutaneous administration preparation, may be in any dosage forms, as long as they can be percutaneously administered to a mammal (e.g., a human, a non-human animal or the like, preferable a human (a patient)). Examples of the percutaneous administration preparation to be used in the present invention include liquid sprays, lotions, ointments, creams, gels, sols, aerosols, cataplasms, plasters and tapes. In these compositions, (2R)-2-propyloctanoic acid or a salt thereof and an oil base which is generally used in external preparations [e.g., a plant oil (e.g., cotton seed oil, sesame oil, olive oil or the like), waxes (e.g., carnauba wax, beeswax or the like), higher hydrocarbons (e.g., white petrolatum, liquid paraffin, plastibase or the like), a fatty acid (e.g., stearic acid, palmitic acid or the like) and an ester thereof, higher alcohols, (e.g., cetanol or the like), silicons (e.g., silicon fluid, silicon gum or the like) or the like], a water-soluble base [e.g., polyvinyl alcohol, carboxyvinyl polymer, a solution or high molecular hydrogel of cellulose derivative or the like, polyethylene glycol (macrogol), a polyethylene glycol-polypropylene glycol copolymer, propylene glycol, 1,3-butylene glycol, ethanol, glycerol or the like], an adhesive to be used in tapes [e.g., a synthetic rubber adhesive (e.g., a methacrylic acid ester copolymer, a natural rubber adhesive, a synthetic isoprene or the like), a silicon polymer adhesive or the like], a film base [e.g., polyethylene, polypropylene, a polyethylene-vinyl acetate copolymer, PET, an aluminum laminate or the like], a gel base [e.g., dry agar, gelatin, aluminum hydroxide, silicic acid or the like], or an emulsion base in which a surfactant [e.g., an anionic surfactant (e.g., a fatty acid, saponin, fatty acid sarcoside, an alcohol sulfuric acid ester, an alcohol phosphoric acid ester or the like), a cationic surfactant (e.g., a quaternary ammonium salt, a heterocyclic amine or the like), an ampholytic surfactant (e.g., an alkyl betaine, lysolecithin or the like), a nonionic surfactant (e.g., a polyoxyethylene alkyl ether, a polyoxyethylene sorbitan fatty acid ester, a sucrose fatty acid ester or the like), or the like] or the like are added to the oil base and water-soluble base, and the like are used. Also, as occasion demands, generally used additive agents, such as a surfactant [e.g., an anionic surfactant (e.g., a fatty acid, saponin, fatty acid sarcoside, an alcohol sulfuric acid ester, an alcohol phosphoric acid ester or the like), a cationic surfactant (e.g., a quaternary ammonium salt, a heterocyclic amine or the like), an ampholytic surfactant (e.g., an alkyl betaine, lysolecithin or the like), a nonionic surfactant (e.g., a polyoxyethylene alkyl ether, a polyoxyethylene sorbitan fatty acid ester, a sucrose fatty acid ester or the like), or the like], a thickener [e.g., a cellulose derivative (e.g., carboxymethylcellulose or the like), a polycarboxylic acid (e.g., polyacrylic acid, a methoxymethylene maleic anhydride copolymer or the like), a nonionic water-soluble polymer (e.g., polyvinyl pyrrolidone, polyvinyl alcohol or the like), a stabilizing agent [e.g., an antioxidant (e.g., ascorbic acid, sodium pyrosulfite or the like), a chelating agent (e.g., EDTA or the like) or the like], a pH adjusting agent [e.g., a phosphate buffer, sodium hydroxide or the like], a preservative [e.g., parabens, an alkyl quaternary ammonium salt (e.g., benzalkonium chloride, benzethonium chloride or the like) or the like], an absorption acceleration auxiliary [e.g., a fatty acid and its esters (e.g., oleic acid, isopropyl myristate or the like), phospholipids (e.g., phosphatidyl choline and the like), terpenes (e.g., limonene or the like), azacycloalkanes (e.g., Azone (trade name, mfd. by Nelson Research) or the like) or the like] and the like can also be added. These percutaneous administration preparations which comprise (2R)-2-propyloctanoic acid or a salt thereof can be produced in the usual way using the aforementioned various bases, adhesives or other additive agents which are added as occasion demands.

The liquid sprays, lotions, sols or aerosols can be produced by dissolving or dispersing (2R)-2-propyloctanoic acid or a salt thereof in solvent such as water, propylene glycol, 1,3-butylene glycol, ethanol and glycerol. Additionally, the aforementioned additive agents can also be added as occasion demands.

The ointments or creams can be produced by mixing (2R)-2-propyloctanoic acid or a salt thereof with the aforementioned water-soluble base, the aforementioned oil base and/or solvent generally used in said technical field such as water or a plant oil, and applying an emulsification treatment by adding a surfactant as occasion demands. Additionally, the aforementioned additive agents can also be added as occasion demands.

The poultice, plasters or tapes can be produced by coating a solution containing (2R)-2-propyloctanoic acid or a salt thereof and the aforementioned adhesive (it may contain the aforementioned additives as occasion demands) on the aforementioned film base and applying a crosslinking treatment and drying operation as occasion demands.

The gels can be produced by pouring a solution containing (2R)-2-propyloctanoic acid or a salt thereof and the aforementioned gel base (it may contain the aforementioned additives as occasion demands) into a mold and applying a crosslinking treatment and drying operation as occasion demands.

When these pharmaceutical compositions are used as an agent for preventing or treating a functional brain disease and/or inhibiting symptom development of the same, administration period of the pharmaceutical compositions may be any period, for example, when its preventive effect is expected, until the onset of functional brain disease is substantially suppressed; for example, when its therapeutic effect is expected, until treatment is substantially completed; or for example when its symptom development inhibitory effect is expected, until the symptom development is substantially inhibited. Also, as occasion demands, these drugs may be intermittently administered by arranging an appropriate cessation interval. In the intermittent administration, it is preferable that the cessation interval is 1 day or more and 30 days or less. For example, it may be an intermittent administration of every other day, an intermittent administration of 2 days administration and 1 cessation interval day, an intermittent administration of 5 days of continuous administration and 2 cessation interval days, or the like, or an intermittent administration which uses a calendar method (for example, the case of tablets is called calendar tablets). Additionally, for example, roughly 2 or 3 times per week of administration is carried out in the case of intrathecal administration.

Examples of the illustrative administration period of the agent of the present invention include, in the case of oral administration or percutaneous administration, from 1 day to 5 years or the like, preferably from 1 day to 1 year or the like, more preferably from 1 day to 6 months or the like and particularly preferably from 1 day to 2 months or the like can be cited. Also, in the case of intravenous administration for example, from 1 day to 100 days and the like, preferably from 1 day to 10 days or the like, more preferably from 1 day to 7 days or the like, most preferably 7 days or the like. Furthermore, in the case of intrathecal administration for example, examples of the illustrative administration period include from 1 day to 3 years or the like, preferably from 1 day to 1 year or the like, more preferably from 1 day to 6 months or the like, most preferably from 1 day to 3 months or the like.

Examples of the administration frequency per day during these administration periods include, in the case of the administration forms of oral administration and intravenous administration, from once to 5 times or the like, preferably from once to 3 times or the like, more preferably from once or twice or the like and most preferably once or the like. In the case of intrathecal administration, although approximately once or twice a day of administration may have no problem, it is more preferable to administer intermittently as described in the foregoing. Additionally, in the case of percutaneous administration, a merit to control blood concentration can be expected. Administration of the agent can be discontinued at the time of generating harmful phenomena, generally called side effects. Therefore, it can also be said to be an administration form which can be easily used by patients.

The pharmaceutical composition to be used in the present invention which comprises (2R)-2-propyloctanoic acid or a salt thereof may be used as a single preparation or can also be used in combination with other agent, a therapeutic method (e.g., counseling or the like) or the like used in treating a functional brain disease.

When a pharmaceutical composition comprising (2R)-2-propyloctanoic acid or a salt thereof is used in combination with other drug, it may be administered as a form of a combination drug in which both components are formulated in one preparation or may be used as a form in which these are administered as separate preparations. The administration as separate preparations includes simultaneous administration and administration in different time. Examples of the other drug to be used in combination include an anxiolytic drug (e.g., a benzodiazepine anxiolytic drug, a thienodiazepine anxiolytic drug, a non-benzodiazepine anxiolytic drug, a serotonin agonist, a CRF antagonist, a tachykinin NK1 antagonist, an MBR ligand or the like), an antidepressant (e.g., a tricyclic antidepressant, a tetracyclic antidepressant, a monoamine releaser, a monoamine oxidase (MAO) inhibitor, a monoamine reuptake inhibitor (SSRI, SNRI), a CRF antagonist, a tachykinin NK1 antagonist, a neurotensin antagonist, a psychoanaleptic, an anxiolytic drug, an antipsychotic drug or the like), an antiparkinsoinism drug (e.g., an anticholinergic agent, a dopamine receptor agonist, a monoamine oxidase (MAO) inhibitor or the like), an antischizophrenic agent (e.g., a dopamine receptor antagonist or the like), an antiepileptic (e.g., a barbituric antiepileptic agent, a hydantoin antiepileptic agent or the like), an antidinic agent, an anti-asthmatic agent (e.g., a bronchodilator, an α receptor agonist, a β2 receptor agonist, a xanthine derivative, an inhalant steroid, an anticholinergic agent, a 5-lipoxygenase inhibitor or the like), an antiulcer agent (e.g., a hostile factor inhibitor, an anti-pepsin drug, an antacid, a histamine H2 receptor blocker, an anti-gastrin drug, a proton pump inhibitor, a muscarinic antagonist, an anticholinergic agent, a protective factor enhancer, a prostaglandin derivative or the like), an antidiarrheal drug (e.g., an antidiarrheal drug, an opioid μ receptor stimulant or the like), a purgative (e.g., a bulk cathartic, a saline cathartic, an irritant cathartic, an affinity polyacrylic resin or the like), a hypotensive drug (e.g., a calcium blocker, a β receptor blocker, an α1 receptor blocker, an angiotensin converting enzyme inhibitor, an angiotensin II receptor antagonist or the like), an antiarrhythmic drug (e.g., a sodium channel blocker, a β receptor blocker, a potassium channel blocker, a calcium blocker or the like), a cardiotonic agent (e.g., a phosphodiesterase inhibitor, a cardiac glycoside, a β receptor agonist or the like), an agent for treating urinary disturbance (e.g., a pollakiuria treating agent, an anticholinergic agent, a muscarinic agonist (antagonist), a tachykinin NK1 antagonist, a NK2 antagonist or the like), a digestive organ function controlling agent and/or a digestive tract movement enhancer (e.g., a antiflatuent, a CCK-A antagonist, a neurotensin antagonist, an opioid receptor agonist, a muscarinic agonist and a 5-HT4 agonist, a 5-HT3 antagonist or the like) or the like.

Examples of the 5-HT3 antagonist include alosetron (hydrochloride) or the like.

Examples of the 5-HT4 agonist include tegaserod (maleate), Cisapride, mosapride citrate or the like.

Examples of the al receptor blocker include AIO-8507L, indoramin, urapidil, silodosin, naftopidil, doxazosin mesylate, alfuzosin hydrochloride, tamsulosin hydrochloride, terazosin hydrochloride, bunazosin hydrochloride, prazosin hydrochloride or the like.

Examples of the α receptor agonist include midodrine hydrochloride or the like.

Examples of the β2 receptor agonist include AR-C68397, AR-C89855, KUL-7211, KUR-1246, R,R-formoterol, S-1319, epinephrine, salmeterol xinafoate, tulobuterol, bambuterol, formoterol, formoterol fumarate, levosalbutamol, clenbuterol hydrochloride, dipivefrine hydrochloride, dopexamine hydrochloride, trimetoquinol hydrochloride, pirbuterol hydrochloride, procaterol hydrochloride, mabuterol hydrochloride, ritodrine hydrochloride, meluadrine tartarate, fenoterol hydrobromide, isoproterenol sulfate, orciprenaline sulfate, clorprenaline sulfate, salbutamol sulfate, terbutaline sulfate, hexoprenalinemesyl sulfate or the like.

Examples of the β receptor blocker include timolol maleate, befunolol hydrochloride, carteolol hydrochloride, betaxolol hydrochloride, atenolol, nadolol, nipradilol, pindolol, bisoprolol fumarate, bopindolol malonate, acebutolol hydrochloride, alprenolol hydrochloride, indenolol hydrochloride, oxprenolol hydrochloride, celiprolol hydrochloride, tilisolol hydrochloride, bucumolol hydrochloride, bufetolol hydrochloride, bupranolol hydrochloride, propranolol hydrochloride, betaxolol hydrochloride, metoprolol tartarate, penbutolol sulfate or the like.

Examples of the angiotensin II receptor antagonist include losartan (potassium), candesartan (cilexetil), valsartan, irbesartan, olmesartan (medoxomil), telmisartan or the like.

Examples of the angiotensin converting enzyme inhibitor include alacepril, imidapril hydrochloride, quinapril hydrochloride, temoapril hydrochloride, delapril hydrochloride, benazepril hydrochloride, captopril, trandolapril, perindopril erbumine, enalapril maleate, lisinopril and the like.

Examples of the opioid receptor agonist include opium, opium ipecac powder, opium alkaloids hydrochlorides, opium alkaloids and atropine injection, alkaloids and scopolamine injection, morphine sulfate, morphine hydrochloride, morphine and atropine injection, ethylmorphine hydrochloride, compound oxycodone injection, compound oxycodone and atropine injection, codeine phosphate, dihydrocodeine phosphate, oxymetebanol, cocaine hydrochloride, pethidine hydrochloride, fentanyl citrate, pentazocine, pentazocine hydrochloride, tramadol hydrochloride, butorphanol tartarate, buprenorphine hydrochloride, eptazocine hydrobromide, fentanyl or the like.

Exampled of the calcium blocker include nifedipine, benidipine hydrochloride, diltiazem hydrochloride, verapamil hydrochloride, nisoldipine, nitrendipine, bepridil hydrochloride, amlodipine besilate, lomerizine hydrochloride, efonidipine hydrochloride or the like.

Examples of the xanthine derivative include aminophylline, theophylline, doxophylline, dipamphylline, diprophylline or the like.

Examples of the serotonin agonist include sumatriptan, sumatriptan succinate, zolmitriptan, naratriptan, rizatriptan, rizatriptan benzoate, eletriptan, eletriptan hydrobromide, almotriptan, frovatriptan or the like.

Examples of the thienodiazepine anxiolytic drug include etizolam, clotiazepam or the like.

Examples of the dopamine receptor agonist include L-dopa, amantadine, cabergoline, talipexole, pergolide, pramipexole, bromocriptine or the like.

Examples of the sodium channel blocker include ajmaline, aprindine hydrochloride, amiodarone hydrochloride, disopyramide, disopyramide phosphate, pilsicainide hydrochloride, pirmenol hydrochloride, procainamide hydrochloride, propafenone hydrochloride, flecainide acetate, mexiletine hydrochloride, lidocaine hydrochloride, lidocaine or the like.

Examples of the antiepileptic include acetazoplamide, acetylpheneturide, ethosuximide, ethotoin, carbamazepine, clonazepam, clobazam, diazepam, sultiame, zonisamide, trimethadione, nitrazepam, valproate, sodium valproate, phenytoin, phenobarbital, phenobarbital sodium, primidone, metharbital, mephobarbital, a carbonic anhydrase inhibitor or the like.

Examples of the histamine H2 receptor blocker include famotidine, ranitidine, cimetidine, roxatidine or the like.

Examples of the prostaglandin derivative include ornoprostil, misoprostol, enprostil or the like.

Examples of the proton pump inhibitor include omeprazole, lansoprazole, rabeprazole sodium or the like.

Examples of the benzodiazepine anxiolytic drug include alprazolam, oxazepam, oxazolam, cloxazolam, clorazepate dipotassium, chlordiazepoxide, diazepam, tofisopam, triazolam, prazepam, fludiazepam, flutazolam, flutoprazepam, bromazepam, mexazolam, medazepam, ethyl loflazepate, lorazepam or the like.

Examples of the phosphodiesterase inhibitor include cilomilast (trade name "Ariflo") (Pre-reg; 200408, IDdb3), roflumilast (BY-217)(Pre-reg; 200408, IDdb3), arofylline (PIII; 200408, IDdb3), OPC-6535 (PIII; 200408, IDdb3), ONO-6126 (PII; 200408, IDdb3), IC-485 (PII; 200408, IDdb3), AWD-12-281 (PII; 200408, IDdb3), CC-10004 (PII; 200408, IDdb3), CC-1088 (PII; 200408, IDdb3), KW-4490 (PII; 200408, IDdb3), Lirimilast (PII; 200408, IDdb3), ZK-117137 (PII; 200408, IDdb3), YM-976 (PI; 200408, IDdb3), BY-61-9987 (PI; 200408, IDdb3), CC-7085 (PI; 200408, IDdb3), CDC-998 (PI; 200408, IDdb3), MEM-1414 (PI; 200408, IDdb3), ND-1251 (PI; 200408, IDdb3), Bay 19-8004, D-4396, PD-168787, Atizoram (CP-80633) (NoDevRep; 200408, IDdb3), Cipamfylline (BRL-61063) (NoDevRep; 200408, IDdb3), Rolipram (Discontinued; 200408, IDdb3), NIK-616 (Discontinued; 200408, IDdb3), SCH-351591 (Discontinued; 200408, IDdb3), V-11294A (Discontinued; 200408, IDdb3) or the like.

Examples of the muscarinic antagonist include pirenzepine or the like.

Examples of the monoamine oxidase (MAO) inhibitor include safrazine hydrochloride, selegiline hydrochloride, deprenyl, riluzole, remacemide or the like.

Examples of the monoamine reuptake inhibitor (SSRI, SNRI) include trazodone (hydrochloride), fluvoxamine (maleate), milnacipran (hydrochloride) or the like.

Examples of the saline cathartics include magnesium sulfate, magnesium oxide or the like.

Examples of the inhalant steroid include beclomethasone dipropionate, fluticasone propionate, budesonide, flunisolide, triamcinolone, ciclesonide, dexamethasone paromitionate, mometasone furoate, prasterone sulfonate, deflazacort, methylprednisolone suleptanate, methylprednisolone sodium succinate, ST-126P or the like.

Examples of the anti-gastrin drug include proglumide, oxethazaine or the like.

Examples of the anticholinergic agent include trihexyphenidyl, trihexyphenidyl hydrochloride, biperiden, biperiden hydrochloride or the like.

Examples of the anti-pepsin drug include sucralfate or the like.

Examples of the antipsychotic drug include clofekton, spiperone, sulpiride, zotepine, timiperone, haloperidol decanoate, fluphenazine decanoate, haloperidol, pimozide, propericiazine, bromperidol, perphenazine, levomepromazine maleate, chlorpromazine hydrochloride, thioridazine hydrochloride, trazodone hydrochloride, mosapramine hydrochloride, a serotonin dopamine antagonist or the like.

Examples of the anxiolytic drug include γ-oryzanol, alprazolam, etizolam, oxazepam, oxazolam, tandospirone citrate, cloxazolam, clotiazepam, clorazepate dipotassium, chlordiazepoxide, diazepam, tofisopam, triazolam, hydroxyzine pamoate, hydroxyzine hydrochloride, prazepam, fludiazepam, flutazolam, flutoprazepam, flunitrazepam, bromazepam, mexazolam, medazepam, ethyl loflazepate, lorazepam or the like.

Examples of the antidinic agent include diphenhydramine salicylate, difenidol, difenidol hydrochloride, betahistine, betahistine mesilate, perphenazine, perphenazine hydrochloride, chlorpromazine hydrochloride, sodium bicarbonate or the like.

Examples of the tricyclic antidepressant include amitriptyline hydrochloride, amitriptyline, imipramine hydrochloride, imipramine, clomipramine hydrochloride, clomipramine, dosulepin hydrochloride, nortriptyline hydrochloride, nortriptyline, lofepramine hydrochloride, trimipramine maleate, amoxapine, desipramine hydrochloride, desipramine or the like.

Examples of the irritant cathartic include picosulfate, lactulose, castor oil, senna, rhubarb or the like.

Examples of the tetracyclic antidepressant include mianserin hydrochloride, mianserin, maprotiline hydrochloride, maprotiline, setiptiline maleate or the like.

Examples of the antacid include aluminum silicate, dried aluminum hydroxide gel, magnesium oxide, sodium bicarbonate, calcium carbonate or the like.

Examples of the psychoanaleptic include methylphenidate hydrochloride, pemoline or the like.

Examples of the non-benzodiazepine anxiolytic drug include tandospirone citrate, hydroxyzine hydrochloride or the like.

Examples of the bulk cathartic include methyl cellulose, carmellose, lactulose or the like.

Examples of the protective factor enhancer include L-glutamine, sodium azulene sulfonate, aceglutamide aluminum, sodium alginate, aldioxa, ecabet sodium, egualen sodium, enprostil, ornoprostil, gefarnate, sucralfate, sulpiride, sofalcone, teprenone, troxipide, plaunotol, polaprezinc, irsogladine maleate, misoprostol, methylmethionine sulfonium chloride, clebopride malate, rebamipide, cetraxate hydrochloride, benexate hydrochloride betadex or the like.

The aforementioned drugs to be used in combination with the pharmaceutical composition comprising (2R)-2-propyloctanoic acid or a salt thereof are examples and not limited thereto. Administration method of these drugs to be used in combination is not particularly limited and may be either oral administration or parenteral administration. Additionally, these drugs may be administered in combination with two or more optional species. Not only those which have so far been found based on the above-mentioned mechanism but also those which will be found in the future are included in these drugs.

Pharmacological Tests

As pharmacological tests other than those which are described in Examples, for example, there are methods shown in the following. By these methods, effects of the (2R)-2-propyloctanoic acid or a salt thereof on functional brain diseases can be proved. To the following methods, modifications for improving accuracy and/or sensitivity of evaluation can be added by examining various test conditions, in order to proper evaluation of pharmacological activity of the (2R)-2-propyloctanoic acid or a salt thereof.

TEST EXAMPLE

Water-Immersion Stress-Loaded Elevated Plus Maze Test

Two open arms of the same length (50×10 cm) and two closed arms of the same length (50×10 cm) (a wall of 30 cm is set) are set crossing at a right angle at a height of 50 cm from the floor and used as an elevated plus maze apparatus. Constant lighting is effected by attaching white lights to 70 cm over both of the open arms.

Using a pool (40×30×38 cm) charged with water of 22° C. to a depth of 25 cm, 120 seconds of forced swimming is loaded on SD rats of 7 weeks of age (Charles River Japan). After 9 minutes of the water-immersion stress-loading, the rats are allowed to stand still on a central part of the apparatus, and the behavior of the rats are analyzed for 5 minutes by an automatic behavior tracing analysis system (EthoVision Version 3.0, Noldus Information Technology) to calculate its staying time (second) on the open arms.

In this connection, rats of the control group are not subjected to the water-immersion stress-loading. Also, a vehicle is orally administered to the vehicle treating group 1 hour before the commencement of the test, and a test drug of various concentrations is administered to the test drug treating group.

As a result, the (2R)-2-propyloctanoic acid as a test drug prolongs the staying time on the open arms in comparison with the vehicle treating group. Based on this result, it can be proved that (2R)-2-propyloctanoic acid has the anxiolytic activity.

TEST EXAMPLE 2

Confirmation Test of Anti-Stress Activity

A psychological stress is loaded on Wistar male rats using the method of B. Bonaz (Brain Res., vol. 641, pp. 21-28, 1994. Water is charged to a depth of about 10 cm in a container which has a platform at the center. The stress loading is started 30 minutes after oral administration of the vehicle or the test drug, and the number of defecations is counted 1 hour thereafter. The rats with no administration and stress loading hardly show defecations. On the other hand, significant defecations are found in the stress-loaded group treated by vehicle. However, the (2R)-2-propyloctanoic acid as a test drug significantly suppress the number of defecations in comparison with the vehicle treating group. Based on this result, it can be proved that (2R)-2-propyloctanoic acid has the anti-stress activity.

TEST EXAMPLE 3

Rat Learned Helplessness Test

A learned helplessness test is carried out using a two way type shuttle box which is divided into two by a gate which can be opened and closed so that shift to right and left is possible. Wistar male rats are used in the test, and a shock training is carried out on the $1^{st}$ day of the test. The shock training is carried out by putting the rats in the apparatus under an inescapable condition by closing the gate, and applying an electric shock (10 seconds×90 times, intervals of 2 seconds) through a floor grid. In this connection, the rats of the control group are not treated with the electric shock and allowed to stay free in the apparatus for the same period of time. An escape test is carried out after 24 hours of the shock training. The escape test is carried out by putting the rats in the apparatus under an escapable condition by opening the gate, and after 5 minutes of adaptation, by applying a light stimulation and a sound stimulation (conditional stimulation) simultaneously for 5 seconds and subsequently applying an electric shock (no conditional stimulation) for 10 seconds. By regarding a case of no escaping and continuously receiving the electric shock as escape failure, this trial is repeated 40 times (intervals of 5 seconds), and behavior of the rats is analyzed by a behavior analysis software (MED-PC Version 1.16).

In this connection, the vehicle and test drug are orally administered once a day for 6 days and further administered 1 hour before the shock training on the $7^{th}$ day.

As a result, the (2R)-2-propyloctanoic acid as a test drug inhibits increase of the number of escape failures which is found in the vehicle treating group. Based on the result, it can be proved that (2R)-2-propyloctanoic acid has the anti-depression activity.

TEST EXAMPLE 4

Examination of Anti-Depression and Anxiolytic Activities in Olfactory Bulbectomized Rats <4-1> Preparation of Olfactory Bulbectomized Rats Wistar male rats are used in the test. By fixing the head of each rat under pentobarbital sodium anesthesia to a brain stereotaxic apparatus, the head skin is incised and then holes are opened at right and left olfactory bulb regions using a dental drill to suck and remove the right and left olfactory bulbs using an aspirator. The head skin is stitched thereafter. In this connection, the suction and removal of olfactory bulbs are not carried out in the sham-operation group, and the head skin is stitched after opening holes at right and left olfactory bulb regions. The rats after extraction of the olfactory bulbs are put into a series of five stainless steel cages, each of which is partitioned into two parts with an acrylic board for individual rearing space, and individually reared for 2 weeks under a dark condition, and then subjected to the following tests of <4-2> and <4-3>.

<4-2> Influence on Hyperemotional Score

The vehicle and test drug are orally administered once a day repeatedly for 7 days. The evaluation is carried out under a quiet environment, before the grouping and on the $1^{st}$ and $7^{th}$ days after administration of the test drug. The degree of irritability is scored in accordance with the evaluation criteria shown below, before the grouping and before the administration of 7 days test drug administration, and after 1 hour of the administration of test drug administration of 1 day and 7 days.

(Evaluation Criteria for Hyperemotionality)

A: Reaction to a rod pushed out toward the nose (0: no reaction, 1: interest on the object, 2: protective or evasive behavior for the object, 3: offensive behavior such as biting, 4: vigorous offensive behavior);

B: Reaction when air is blown (0: no reaction, 1: the body merely moves slightly, 2: astonished reaction, 3: shows a significant astonished reaction bur does not jump, 4: shows a significant astonished reaction and jumps);

C: Resistance to capture and handling (0: no resistance, significant muscular relaxation, 1: capturing and handling are easy, 2: capturing and handling are easy, but a slight muscular tension, 3: shows a muscular tension, capturing and handling are difficult to perform, 4: capturing is markedly difficult, considerable muscular tension);

D: Reaction when the tail is pinched with a forceps (0: no reaction, 1: interest on the object, 2: protective or evasive behavior for the object, 3: offensive behavior such as biting, 4: vigorous offensive behavior);

E: Squeak during the tests (A to D) (0: no squeak, 1: sometimes squeaks, 2: violently squeaks).

As a result, the (2R)-2-propyloctanoic acid as a test drug inhibits development of hyperemotionality which is found in the group treated with vehicle. Based on the result, it can be proved that (2R)-2-propyloctanoic acid has the anti-depression activity.

<4-3> Influence Upon Anxiolytic Behavior on an Elevated Plus Maze

An elevated plus maze apparatus consisting of a open arm without a wall and a closed arm having a wall is used in the test. In this connection, the apparatus is set up a height of 60 cm from the floor. The observation is carried out in a gloomy room. Lightening is adjusted such that the intensity of illumination inside the closed arm becomes about half of that on the open arm. The anxiolytic behavior is analyzed from the pictures of a video camera by a video picture behavior analysis device.

The vehicle and test drug are repeatedly administered once a day for 8 days. The test is carried out on the 8th day after the administration. After 2 hours of the administration, the animal is softly put on the platform toward one of the open arms and measured for 5 minutes. However, when the animal fell, it is regarded as staying on the open arm, and the animal is quickly returned to the place or platform where it was present just before the falling. The items (1) to (6) shown below are measured using the video picture behavior analysis device, and (7) and (8) are counted after completion of the measurement.

(Evaluation Items)

(1) Frequency of approach to the open arm;
(2) Frequency of approach to the closed arm;
(3) Frequency of approach to the center platform;
(4) Stayed time (second) on the open arm;
(5) Stayed time (second) on the closed arm;
(6) Stayed time (second) on the center platform;
(7) Defecation frequency on the open arm, center platform and closed arm;
(8) Urination frequency on the open arm, center platform and closed arm.

As a result, the (2R)-2-propyloctanoic acid as a test drug suppresses the anxiolytic behavior which is found in the vehicle treating group. Based on the result, it can be proved that (2R)-2-propyloctanoic acid has the anxiolytic activity.

Toxicity

It can be assumed that since toxicity of the (2R)-2-propyloctanoic acid or a salt thereof is very low, it is sufficiently safe in using as a medicine. For example, there was no dead case by 100 mg/kg single intravenous administration of (2R)-2-propyloctanoic acid using dogs.

Application to Pharmaceuticals

Features of the present invention are that an effective amount of (2R)-2-propyloctanoic acid or a salt thereof is administered with the aim of preventing or treating functional brain disease and/or inhibiting symptom development of the same. The pharmaceutical composition to be used in the present invention comprising (2R)-2-propyloctanoic acid or a salt thereof contains (2R)-2-propyloctanoic acid or a salt thereof as the active ingredient and can be used for the aforementioned purpose in a mammal (e.g., a human or a non-human animal, e.g., monkey, sheep, cattle, horse, dog, cat, rabbit, rat, mouse or the like). Particularly, when it is systemically administered orally or parenterally to a mammal (e.g., a human, a non-human animal or the like, preferable a human (a patient)) with the proper methods and doses described in the present invention as examples, or topically administered like the case of intrathecal administration and percutaneous administration, for example, preferable effects can be obtained for a functional brain disease represented by depression, menopausal mood disorder, perimenopausal mood disorder, panic disorder, irritable bowel syndrome, social anxiety disorder and post-traumatic stress disorder.

Effect of the Invention

Illustrative methods for the use of (2R)-2-propyloctanoic acid or a salt thereof for preventing or treating a functional brain disease and/or inhibiting symptom development of the same are provided by the present invention. Particularly, when (2R)-2-propyloctanoic acid or a salt thereof is administered by the proper methods and doses shown in the present invention as examples, it can show the effect to prevent or treat and/or inhibit development of symptoms of a functional brain disease represented by depression, menopausal mood disorder, perimenopausal mood disorder, panic disorder, irritable bowel syndrome, social anxiety disorder and post-traumatic stress disorder. For example, as described in the Examples shown in the following, preferable effects for functional brain diseases can be shown.

BEST MODE FOR CARRYING OUT THE INVENTION

Although the following describes the present invention in detail based on examples, the present invention is not limited thereto.

The fact that (2R)-2-propyloctanoic acid or a salt thereof has the activity to prevent or treat a functional brain disease and/or inhibit symptom development of the same was proved by the following test.

The following shows detailed test methods.

EXAMPLE 1

Examination of the Activity of (2R)-2-propyloctanoic Acid for Hyperemotional Reactivity and Anxiolytic Behavior on Elevated Plus Maze of Olfactory Bulbectomized Rat With the aim of evaluating the activity of (2R)-2-propyloctanoic acid for hyperemotional reactivity and anxiolytic behavior on elevated plus maze of olfactory bulbectomized rats, the following tests were carried out.

<Test Methods>

(1) Sham-Operation and Preparation of Olfactory Bulbectomized Animals

SPF rats (Crlj: WI) were used in the test. The animal for olfactory bulbectomy was anesthetized with pentobarbital sodium (Nembutal R Injection, Dainippon Pharmaceutical, dose: 1 mL/kg (intraperitoneal administration)), and the head was fixed using a brain stereotaxic apparatus (ASI Instruments, Inc., NARISHIGE). After incising the head skin, holes are opened at right and left olfactory bulb regions of the skull using a dental drill (manufactured by MINI-TOR), and the right and left olfactory bulbs were removed by sucking them using an aspirator connected to a tip-removed oral sonde, and the head skin was stitched thereafter. In this connection, in the case of the animals for sham-operation, anesthesia, brain fixation and head skin incision were carried out in the same manner as in the animals for olfactory bulbectomy, holes are opened at right and left olfactory bulb regions of the skull and the head skin was stitched without carrying out suction removal of the olfactory bulbs. The rats after olfactory bulbectomy were put into a series of five stainless steel cages, each of which was partitioned into two parts with an acrylic board for individual rearing space, and individually reared under a dark condition. The rats were subjected to the following tests of (2) and (3).

In this connection, the group constitution and drug administration method are as shown in the following.

[Group Constitution]
(a) Sham-operation group (12 animals);
(b) Vehicle control group (12 animals);
(c) 3 mg/kg administration group (12 animals) of (2R)-2-propyloctanoic acid;
(d) 10 mg/kg administration group (12 animals) of (2R)-2-propyloctanoic acid;
(e) 10 mg/kg administration group (12 animals) of Milnacipran hydrochloride.

[Drug Administration]

As shown below, drug solution or vehicle was administered once a day for 8 days, a total of 8 times, at a respective liquid dose of 5 mL/kg.
(a) Sham-operation group: vehicle (0.1% by volume Tween 80) aqueous solution;
(b) Vehicle control group: vehicle (0.1% by volume Tween 80) aqueous solution;
(c) 3 mg/kg administration group of (2R)-2-propyloctanoic acid: a drug solution in which (2R)-2-propyloctanoic acid was prepared to be 0.6 mg/mL with the vehicle;
(d) 10 mg/kg administration group of (2R)-2-propyloctanoic acid: a drug solution in which (2R)-2-propyloctanoic acid was prepared to be 2.0 mg/mL with the vehicle;
(e) 10 mg/kg administration group of milnacipran hydrochloride: a drug solution in which Milnacipran hydrochloride was prepared to be 2.3 mg/mL with the vehicle (Milnacipran itself is included in 2.0 mg/mL).

(2) Examination of the Activity for Hyperemotional Reactivity

<Evaluation Method>

Evaluation of the hyperemotional reactivity was carried out (1) before the grouping, (2) from 1 hour to 1 hour and 10 minutes after administration of the 1 day drug administration, (3) before administration of the 7 days administration and (4) from 1 hour to 1 hour and 10 minutes after the administration (a total of 4 times), by scoring the degree of irritability once a rat in accordance with the following evaluation criteria of hyperemotional reactivity (hyperemotional score: prepared based on the method of Gomita et al. (Folia Pharmacologica Japonica, 82, 267, 1983). Additionally, all of the conditions of the evaluation were shot and recorded using a video camera (SSC-DC430, SONY) and handled as reference data.

[Evaluation Criteria of Hyperemotional Reactivity]

A: Reaction to a rod pushed out toward the nose (0: no reaction, 1: interest on the object, 2: protective or evasive behavior for the object, 3: offensive behavior such as biting, 4: vigorous offensive behavior);

B: Reaction when air is blown (0: no reaction, 1: the body merely moves slightly, 2: astonished reaction, 3: shows a significant astonished reaction bur does not jump, 4: shows a significant astonished reaction and jumps);

C: Resistance to capture and handling (0: no resistance, significant muscular relaxation, 1: capturing and handling are easy, 2: capturing and handling are easy, but a slight muscular tension, 3: shows a muscular tension, capturing and handling are difficult to perform, 4: capturing is markedly difficult, considerable muscular tension);

D: Reaction when the tail is pinched with a forceps (0: no reaction, 1: interest on the object, 2: protective or evasive behavior for the object, 3: offensive behavior such as biting, 4: vigorous offensive behavior);

E: Squeak during the tests (A to D) (0: no squeak, 1: sometimes squeaks, 2: violently squeaks).

<Results>

The (2R)-2-propyloctanoic acid inhibited development of hyperemotionality which is found in the vehicle control group of the olfactory bulbectomized rats. The (2R)-2-propyloctanoic acid inhibited development of hyperemotionality which is found in the vehicle control group, 1st day of the administration and the 7th day of the administration. Namely, it was found that (2R)-2-propyloctanoic acid shows its efficacy by its single administration and also by continuous administration. Therefore, (2R)-2-propyloctanoic acid has the excellent effect to prevent or treat mood disorders such as depression and/or to inhibit symptom development of the same.

TABLE 1

Activity of (2R)-2-propyloctanoic acid on hyperemotional reactivity

| | | Hyperemotional score (mean ± S. E.) | | | |
| | | One day administration | | Seven days administration | |
| Group constitution | Dose (mg/kg) | Before administration | After administration | Before administration | After administration |
| --- | --- | --- | --- | --- | --- |
| Sham-operation group | — | 2.8 ± 0.1 | 3.6 ± 0.3 | 3.0 ± 0.1 | 3.5 ± 0.2 |
| Vehicle control group | — | 20.0 ± 0.0 | 20.8 ± 0.3 | 21.2 ± 0.3 | 21.7 ± 0.4 |
| (2R)-2-propyloctanoic acid | 3 | 20.0 ± 0.0 | 8.8 ± 1.4 | 6.3 ± 1.0 | 5.9 ± 1.5 |

TABLE 1-continued

Activity of (2R)-2-propyloctanoic acid on hyperemotional reactivity

| | | Hyperemotional score (mean ± S. E.) | | | |
|---|---|---|---|---|---|
| | | One day administration | | Seven days administration | |
| Group constitution | Dose (mg/kg) | Before administration | After administration | Before administration | After administration |
| administration group | 10 | 20.0 ± 0.0 | 7.4 ± 0.9 | 6.7 ± 1.4 | 4.8 ± 0.8 |
| Milnacipran hydrochloride administration group | 10 | 20.0 ± 0.0 | 14.3 ± 1.0 | 10.2 ± 1.1 | 7.6 ± 0.8 |

(3) Examination of the Action for Anxiolytic Behavior on an Elevated Plus Maze

<Evaluation Method>

Evaluation of the anxiolytic behavior on an elevated plus maze was carried out once per animal for 5 minutes from 1 hour to 1 hour and 10 minutes after 8 days of the administration, in accordance with the following method. Each animal was softly put on a platform of elevated plus maze which is described later, toward one of the open arms. Thereafter, behavior of the animal was shot using a video camera (CCD-DC430, SONY) set up the elevated plus maze, and the images were analyzed by a video image behavior analyzing device (Etho Vision, manufactured by Noldus). Additionally, the images from the video camera were recorded and handled as reference data. In this connection, when the animal fell, it was regarded as staying on the open arm, and the animal was quickly returned to the place or the open arm where it was present just before the falling. The evaluation was carried out on the respective items shown by A to H (A: frequency of approach to the open arm, B: frequency of approach to the closed arm, C: frequency of approach to the platform, D: stayed time (second) on the open arm, E: stayed time (second) on the closed arm, F: stayed time (second) on the platform, G: defecation frequency on the open arm, platform and closed arm, and H: urination frequency on the open arm, platform and closed arm), by measuring A to F using the video image behavior analyzing device, and by measuring G and H after completion of the measurement.

[Elevated Plus Maze]

An elevated plus maze consisting of an open arm without a wall and a closed arm having a wall, in which the bottom of each arm was painted black, and the sides thereof white, was used. Regarding the size of the elevated plus maze, the length was 42 cm and width was 15 cm for both of the open arm and closed arm. Height of the wall of the closed arm was 30 cm, and the apparatus was set up a height of 60 cm from the floor. When the test was carried out, brightness of the room was set to such a level that the intensity of illumination on the elevated plus maze became from 4 to 30 Lux.

<Results>

The (2R)-2-propyloctanoic acid inhibited the anxiolytic behavior which is found in the vehicle control group of olfactory bulbectomized rats. Among the obtained results, the stayed time (seconds) on the open arm and the stayed time (seconds) on the closed arm are shown in the following Table 2. On each item, (2R)-2-propyloctanoic acid inhibited the anxiolytic behavior which is found in the vehicle control group. Accordingly, it was found that (2R)-2-propyloctanoic acid has the excellent effect to prevent or treat anxiolytic disorders and/or to inhibit symptom development thereof.

TABLE 2

Activity of (2R)-2-propyloctanoic acid for the anxiolytic behavior on the elevated plus maze

| Group constitution | Dose (mg/kg) | Time (seconds) stayed on open arm (mean ± S. E.) | Time (seconds) stayed on closed arm (mean ± S. E.) |
|---|---|---|---|
| Sham-operation group | — | 103.4 ± 18.5 | 120.7 ± 16.0 |
| Vehicle control group | — | 19.0 ± 9.7 | 254.0 ± 13.0 |
| (2R)-2-propyl-octanoic acid administration group | 3 | 73.7 ± 17.5 | 188.7 ± 19.7 |
| | 10 | 57.7 ± 22.1 | 209.4 ± 24.1 |
| Milnacipran hydrochloride administration group | 10 | 72.7 ± 18.3 | 196.0 ± 19.8 |

PREPARATION EXAMPLE 1

Production of Injections Containing (2R)-2-propyloctanoic Acid

To water for injection, (2R)-2-propyloctanoic acid (2.0 kg) and sodium triphosphate.12H$_2$O (3.54 kg) were added and adjusted to 40 liters using water for injection. After making into a uniform solution, filtration through a sterile filter (Durapore 0.22 μm membrane); filling into plastic ampoules in 2 mL portions; and autoclaving (123° C., 15 minutes) were carried out to obtain 20,000 ampules containing 100 mg of the active ingredient in 1 ampoule.

PREPARATION EXAMPLE 2

Production of (2R)-2-propyloctanoic Acid-Containing Soft Capsules

Gelatin (20 kg) and concentrated glycerol (6 kg) were mixed at 70° C. in the presence of purified water (20 kg) to obtain a uniform solution. The solution and (2R)-2-propyloctanoic acid (0.9 kg) were put into a soft capsule filling machine (a rotary type soft capsule molding machine Model H-1; Kamata) to obtain "capsules before drying" of soft capsules filled with (2R)-2-propyloctanoic acid. By subjecting the thus obtained "capsules before drying" to tumbler drying and shelf drying in order, soft capsules (2200 capsules) containing 300 mg of (2R)-2-propyloctanoic acid in one capsule were obtained.

INDUSTRIAL APPLICABILITY

The "agent for preventing or treating a functional brain disease and/or inhibiting symptom development of the same, which comprises (2R)-2-propyloctanoic acid or a salt thereof" disclosed by the present invention is very useful as pharmaceuticals, since it can be safely administered to patients of, for example, functional cerebral disorders such as depression, menopausal mood disorder, perimenopausal mood disorder, panic disorder, irritable bowel syndrome, social anxiety disorder, post-traumatic stress disorder or the like, and also shows excellent preventive, therapeutic and/or symptom development inhibitory effect. Additionally, since it is possible also to use the "agent for preventing or treating a functional brain disease and/or inhibiting symptom development of the same, which comprises (2R)-2-propyloctanoic acid or a salt thereof" disclosed by the present invention in combination with conventionally used existent drugs, it can also be administered to patients who are already using existent drugs.

The invention claimed is:

1. A method for treating a functional brain disease and/or inhibiting symptom development of the same, which comprises administering an effective amount of (2R)-2-propyloctanoic acid or a salt thereof to a mammal in need thereof, wherein said functional brain disease is anxiety disorder.

2. The method according to claim 1, wherein the effective amount of (2R)-2-propyloctanoic acid or a salt thereof is 1 mg to 5000 mg.

3. The method according to claim 1, wherein the anxiety disorder is panic disorder, social anxiety disorder and/or post-traumatic stress disorder.

4. The method according to claim 1, wherein the (2R)-2-propyloctanoic acid or a salt thereof is used in combination with an anxiolytic drug.

* * * * *